United States Patent [19]

Edelman et al.

[11] 4,282,122

[45] Aug. 4, 1981

[54] LIQUID MODIFIED EPOXY RESINS

[75] Inventors: Leonard E. Edelman; Robert H. Runk, both of Pittsburgh, Pa.

[73] Assignee: Westinghouse Electric Corp., Pittsburgh, Pa.

[21] Appl. No.: 614,717

[22] Filed: Sep. 17, 1975

Related U.S. Application Data

[63] Continuation of Ser. No. 180,873, Sep. 15, 1971, abandoned, which is a continuation-in-part of Ser. No. 845,405, Jul. 28, 1969, abandoned.

[51] Int. Cl.$^3$ ........................... C09D 3/30; C09D 3/58
[52] U.S. Cl. ............................. 260/18 EP; 260/22 EP
[58] Field of Search ............. 260/18 EP, 47 EP, 462, 260/22 EP

[56] References Cited

U.S. PATENT DOCUMENTS

| | | | |
|---|---|---|---|
| 2,941,981 | 6/1960 | Elbling et al. | 260/47 EP |
| 2,953,545 | 9/1960 | Finestone | 260/47 EP |
| 2,970,130 | 1/1961 | Finestone | 260/47 EP |
| 3,012,485 | 12/1961 | Bradley | 94/22 |
| 3,051,671 | 8/1962 | Cummings | 260/18 EP |
| 3,219,602 | 11/1965 | Scheibli | 260/18 EP |
| 3,380,963 | 4/1968 | Thomas | 260/47 EP |

FOREIGN PATENT DOCUMENTS

| | | | |
|---|---|---|---|
| 205972 | 3/1956 | Australia | 260/18 EP |
| 518956 | 11/1955 | Canada | 260/18 EP |
| 714605 | 7/1965 | Canada | 260/18 EP |
| 1317658 | 5/1973 | United Kingdom . | |

*Primary Examiner*—Ronald W. Griffin
*Attorney, Agent, or Firm*—R. D. Fuerle

[57] ABSTRACT

Liquid modified epoxy resins are prepared by reacting a drying oil with a diepoxide in the presence of a metal chelate catalyst. The drying oil may be modified by reacting it with maleic acid, maleic anhydride, or fumaric acid to increase the drying rate. The catalyst may be modified by mixing or reacting it with a borate.

22 Claims, No Drawings

LIQUID MODIFIED EPOXY RESINS

CROSS-REFERENCE TO RELATED APPLICATION

This application is a continuation of application Ser. No. 180,873 filed Sept. 15, 1971, now abandoned, which in turn is a continuation-in-part of our copending application Ser. No. 845,405 titled "Drying-Oil-Modified Liquid Epoxy Resins" filed July 28, 1969 and now abandoned.

BACKGROUND OF THE INVENTION

An epoxy resin may be in the form of a liquid or of a solid, depending on its epoxy equivalent weight. A solid epoxy resin may be used for coatings by applying a solution of it to an object and evaporating the solvent (see Australian Pat. No. 205,972) or by melting a catalyzed powder on the object. But it is not practical to use a solid epoxy resin as a potting or casting compound since a solvent cannot evaporate from deep within the casting and a melt of the resin would tend to polymerize prematurely.

While liquid epoxy resins would therefore be much more suitable as casting and potting compounds than solids resins, until now it has been difficult to control the flexibility of liquid epoxy resins. Plasticizers have been tried but they are extractable and the resin gradually becomes less and less flexible. Flexible hardeners have also been tried but they are expensive and give only a narrow range of flexibility.

While drying oils are easily made compatible with solid epoxies (see Canadian Pat. No. 518,956 and Australian Pat. No. 205,972), efforts to incorporate drying oils into liquid epoxy resins to flexibilize them have failed to produce a clear resin.

SUMMARY OF THE INVENTION

We have discovered that a certain class of metal chelate catalysts will enable drying oils to react with diepoxides to produce liquid modified epoxy resins which are curable to give a wide range of flexibilities, from a near-liquid to a rigid solid. The modified epoxy resins of this invention are relatively inexpensive and are useful as potting and casting compounds, for forming coatings, and purposes for which other epoxy resins are used. They are very stable and resist gelation for several months when stored at room temperature in a tight-lidded container.

DESCRIPTION OF THE INVENTION

In this invention about 20 to about 80% (all percentages herein are by weight) of at least one diepoxide is reacted with about 20 to about 80% of at least one drying oil in the presence of at least one metal chelate catalyst. Large amounts of drying oil increase the flexibility of the resin but decrease its strength, and about 40 to about 60% diepoxide and about 40 to about 60% drying oil will produce a resin useful for most purposes. If the amount of catalyst is insufficient, the reaction will not proceed at a practical rate and if it is too great the diepoxide will cure before it reacts with the drying oil; about 0.1% to about 1.5% (based on the diepoxide plus drying oil) is usually satisfactory.

The reaction should preferably be performed under a blanket of an inert gas such as nitrogen to exclude oxygen which tends to thicken the resin by reacting with the drying oil. The diepoxide, drying oil, and catalyst are heated under non-hydrolyzing conditions (to preserve the epoxy functionality) at about 200° to about 250° C. until the clear-pill stage is reached (i.e., the point at which a sample, cooled to room temperature, is clear and not cloudy) which is usually in about ½ to 1½ hours. Lower temperatures require impractically long reaction times and higher temperatures may gel the drying oil. The reaction may be continued beyond the clear-pill stage if higher viscosities are desired. Also, a lack of clarity may result with the use of certain curing agents, such as polyamides, and this can be eliminated by heating for about a half-hour beyond the clear-pill stage.

The liquid modified epoxy resin thus formed may then be mixed reactive diluents, fillers, thixotropic agents, reinforcing material, pigments, etc. as is known in the art. A curing agent is mixed in, and the resin is poured on a substrate or into a mold and is cured.

THE DIEPOXIDES

The diepoxides of this invention are diglycidyl ethers of diphenols of the formula $$CH_2-CH-CH_2+R'-CH_2-CHOH-CH_2\!\!\mid_n\!\!R'-CH_2-CH-CH_2$$
$$\diagdown\!\!O\!\!\diagup \qquad\qquad\qquad\qquad\qquad\qquad \diagdown\!\!O\!\!\diagup$$

where R' is a diphenol radical such as 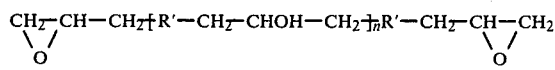 or

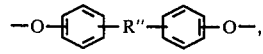, where R" is $-CH_2-$, $-O-$, $-\overset{CH_3}{\underset{CH_3}{\overset{|}{\underset{|}{C}}}}-$, or or 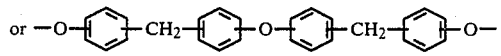

and n is an average of less than 1 and preferably is an average of about 0. These low values of n are required in order for the diepoxide to be a liquid, which is necessary if the modified epoxy resin product is to be a liquid. It should be noted that n is an average value and commercially about 75 to 98% of the diglycidyl ether will have the exact value of n equal to 0 and the remaining 2 to 25% will be higher values of n. The preferred diphenol is bisphenol A (4,4'-dihydroxy-diphenyl-dimethyl-metnane) as it is inexpensive and readily available. Examples of other suitable diphenols include resorcinol, which produces less viscous resins than does bisphenol A, hydroquinone, and pyrogallol.

THE DRYING OIL

The drying oils of this invention lack hydroxyl functionality (which would etherify with the epoxy groups) and are typically natural products which are triglycerides of mixed unsaturated fatty acids. While natural drying oils are preferred due to their availability, drying oils may be prepared synthetically by stochiometrically reacting a fatty acid of the formula $C_{17}H_xCOOH$, where x is 28 to 33, with a polyhydroxy compound having 2 to 4 hydroxyl groups. Glycerine is the preferred polyhydroxy compound as it is inexpensive and readily available but pentaerythritol, trimethylolethane, trimethylolpropane, ethylene glycol, etc. and mixtures of polyhydroxy compounds could also be used.

Examples of suitable drying oils include linseed oil, oiticica oil, perilla oil, tung oil, dehydrated castor oil, soya oil, safflower oil, and fish oil; linseed oil, either raw or alkali-refined, is preferred as it offers the best compromise of drying properties and cost.

MODIFIED DRYING OILS

If the epoxy resin is to be cured with a curing agent, there is no need to use a modified drying oil. But if the resin is to be cured by exposure to oxygen, it may be desirable to use a modified drying oil which dries faster due to the presence of additional unsaturation.

The drying oil may be modified by reacting it with up to about 10% (based on the drying oil) maleic acid, maleic anhydride, or fumaric acid and about 1 to 1.5 times the amount of maleic acid, maleic anhydride, or fumaric acid, of at least one saturated aliphatic polyhydric alcohol having two to six hydroxyl groups. The presence of up to about 1.5% (based on the drying oil) of an ester-interchange catalyst such as lime is desirable to speed the reaction. The reactants are heated at about 230° C. until an acid value of less than 14 is obtained, which is usually after about ½ to about 2 hours. The acid value is the number of milligrams of KOH required to neutralize 1 gram of the charge and it should be less than 14 in order to avoid excessively high viscosities when the modified drying oil is reacted with the diepoxide. The reaction should be performed under a blanket of inert gas such as nitrogen to prevent oxygen from thickening the drying oil.

Maleic anhydride and pentaerythritol are preferred as they work well and are readily available. Examples of other suitable polyols include dipentaerythritol, trimethylolethane, trimethylolpropane, glycerine, and ethylene glycol.

THE METAL CHELATE CATALYST

The metal chelate catalyst of this invention has the general formula

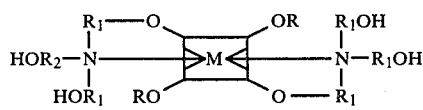

where M is titanium, aluminum, or silicon, preferably titanium as that catalyst is readily available, and works well $R_1$ is ethylene, propylene, or isopropylene and each R is independently selected from aliphatic or cycloaliphatic having 1 to 6 carbon atoms and the aromatic group

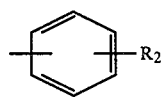

where $R_2$ is hydrogen or alkyl to $C_4$. Preferably both R groups are identical and are alkyl to $C_4$ as those catalysts are easier to prepare.

Examples of suitable catalysts include isopropyl triethanolamine titanate which is preferred because it works well and is readily available, cyclohexyl tripropanolamine titanate, butyl triethanolamine aluminate, phenyl triethanolamine silicate, and tolyl tripropanolamine titanate.

MODIFIED CATALYSTS

To avoid local gelation which may occur with an unmodified catalyst, the catalyst is preferably modified by the addition of at least one borate compound in a ratio of metal chelate to borate of about 1 to 2 to about 2 to 1. (See U.S. Pat. Nos. 2,809,184 and 2,941,981). The catalyst and borate may be used as a mixture or may be pre-reacted to form a compound by heating them to, for example, about 130° to 185° C. for about an hour or until alcohol is no longer evolved. The compound is preferred since human errors are less likely to occur when a larger amount of one ingredient is used instead of smaller amounts of two ingredients.

Suitable borates include compounds of the formulae

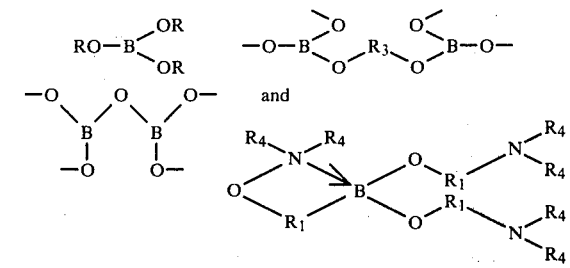

where R and $R_1$ are as previously defined, $R_3$ is a bivalent radical derived from a saturated aliphatic polyhydric alcohol having two to six hydroxyl groups two of which are removed, $R_4$ is hydrogen or R, and the open oxygen bonds are satisfied by $R_3$ or a monovalent radical derived from a monohydric alcohol having one hydroxyl group removed selected from the group consisting of saturated and unsaturated aliphatic, aromatic, and phenolic hydroxyl alcohols.

The preferred borate is trimetaparacresol borate as it has been found to work well and it does not produce volatile byproducts as does, for example, methyl borate. Other examples include di-n-hexylene glycol biborate, tri-hexylene glycol biborate, tri-octylene glycol biborate, methyl borate, etc.

THE MODIFIED EPOXY RESIN PRODUCT

The epoxy resin products of this invention are curable through their epoxy functionalities and have epoxy equivalent weights (E.E.W.) of less than 8000 and preferably of less than 5000 for more epoxy functionality and therefore faster and more complete cures. Their minimum E.E.W. may be expressed as the E.E.W. of the diepoxide divided by the percent of diepoxide in the composition. Their softening points are below about 24° C. and most commonly are below 10° C.

The following examples further illustrate this invention.

EXAMPLE 1

A reaction vessel was charged with 300 gms. commercial diglycidyl ether of bisphenol A sold by Celanese under the trademark "Epirez 510" (n in the formula=about 0.15), 300 gms. raw linseed oil, and 6 gms, isopropyl triethanolamine titanate. The charge was heated to 210°–220° C. with stirring for 1 hour 45 minutes. A clear pill of liquid modified epoxy resin was obtained. It is cured with methyl nadic anhydride and has an E.E.W. of 400–420.

EXAMPLE 2

Example 1 is repeated using diglycidyl ether of resorcinol, tung oil and butyl triethanolamine aluminate. A resin of lesser viscosity is obtained having an E.E.W. of 320–330 which is cured as in Example 1.

EXAMPLE 3

Example 1 is repeated using diglycidyl ether of hydroquinone, perilla oil, and phenyl triethanolamine silicate. A liquid modified epoxy resin is obtained having an E.E.W. of 330–340 which is cured as in Example 1.

EXAMPLE 4

A mixture is made of 305 grams of alkali-refined linseed oil, 605 grams of liquid diglycidyl ether of bisphenol A having an epoxide equivalent weight of 175–210, such as that sold under the designation "Epon 828" by Shell Chemical Co. (n in the formula=about 0.15), and 20 grams of the reaction product of trimetaparacresol borate and isopropyl triethanolamine titanate. The mixture is heated to a temperature of 230° C.–240° C., and at periodic intervals, about every 5 minutes, drops thereof are removed and cooled to room temperature to determine whether they remain clear. After a period of heating of about 1 hour, it is found that the drops being removed from the mixture remain clear upon cooling to room temperature, and heating of the mixture is stopped, so that the mixture is permitted to cool to room temperature. At this point, the mixture comprises a drying-oil modified liquid epoxy-resin composition. This composition has an E.E.W. of 420–430 and is stable when stored for 3 months in a tight-lidded container at room temperature. It is also capable of being cured or hardened with the use of customary curing agents of the anhydride type.

As illustrative of such curing, 20 grams of the aboveindicated liquid oil-modified-epoxy-resin composition are mixed with 4.5 grams of methyl nadic anhydride. Then, upon heating to a temperature of 150° C. and holding at that temperature for a period of 4 hours, a clear, tough flexible solid epoxy resin is obtained.

EXAMPLE 5

A mixture is made of 605 grams of alkali-refined linseed oil, 605 grams of liquid diglycidyl ether of resorcinol having an epoxide equivalent weight of 175–210 (n in the formula=0.12 to 0.15), and 20 grams of tri hexylene glycol biborate and isopropyl triethanolamine titanate. The mixture is heated to a temperature of 230° C.–240° C., and at periodic intervals, about every 5 minutes, drops thereof are removed and cooled. After a period of heating of about 1 hour, it is found that the drops being removed from the mixture remain clear upon cooling to room temperature. Heating of the mixture is then continued for an additional 30 minutes, after which the mixture is permitted to cool to room temperature. At this point, the mixture comprises a drying-oil-modified liquid epoxy-resin composition having an E.E.W. of 420–430. This composition is stable when stored for 3 months in a tight-lidded container at room temperature. It is also capable of being cured or hardened with the use of customary curing or hardening agents.

To 85 grams of the above mixture, there are added 15 grams of a fatty-acid polyamide resin having an amine value of 290–320 and a viscosity of 40,000 to 60,000 centipoises at 25° C. sold by General Mills under the designation "VERSAMID 125". Upon being placed in an oven at 100° C. and permitted to remain there for about 30 minutes, the mixture cures to a tough, flexible state.

EXAMPLE 6

Example 4 is repeated, except that a 50—50 mixture of the diglycidyl ether of bisphenol A and resorcinol is substituted for the diglycidyl ether of bisphenol A, soybean oil is substituted for an alkali-refined linseed oil, and tri-octylene glycol biborate is substituted for trimetaparacresol borate. The results are the same except that the E.E.W. is 425–435.

EXAMPLE 7

Example 4 is repeated, except that safflower oil is substituted for alkali-refined linseed oil and butyl borate is substituted for trimetaparacresol borate. The results are the same.

EXAMPLE 8

Example 4 is repeated, except that tung oil is substituted for alkali-refined linseed oil and a 32% methanol-68% methyl borate azeotrope is substituted for trimetaparacresol borate. The results are the same.

We claim:

1. A method of making a liquid modified epoxy resin comprising reacting under non-hydrolyzing conditions to the clear pill stage about 20 to about 80% by weight of at least one liquid diglycidyl ether of a diphenol with about 20 to about 80% by weight of at least one non-hydroxylated drying oil in the presence of about 0.1 to about 1.5% by weight (based on the diglycidyl ether and the drying oil) of at least one catalyst having the formula

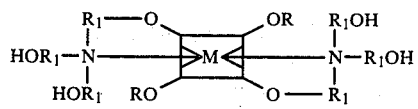

where M is titanium, aluminum, or silicon, $R_1$ is ethylene, propylene, or isopropylene, R is aliphatic or cycloaliphatic having 1 to 6 carbon atoms or

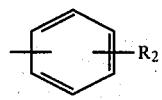

where $R_2$ is hydrogen or alkyl to $C_4$, and said diglycidyl ether of a diphenol has the formula

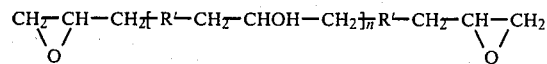

where R' is a diphenol radical selected from the group consisting of

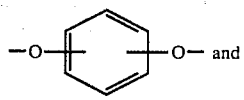 and

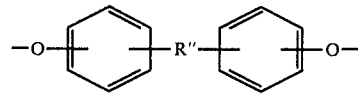

where R" is selected from the group consisting of $-CH_2-$, $-O-$, $\begin{array}{c} CH_3 \\ | \\ -C- \\ | \\ CH_3 \end{array}$ and $$-O-\phenyl-CH_2-\phenyl-O-\phenyl-CH_2-\phenyl-O-$$

n is an average of less than 1.

2. A method according to claim 1 wherein said catalyst is isopropyl triethanolamine titanate.

3. A method according to claim 1 wherein R' is $$-O-\phenyl-R''-\phenyl-O-$$

and R'' is $$\begin{array}{c} CH_3 \\ | \\ -C- \\ | \\ CH_3 \end{array}$$

4. A method according to claim 1 wherein R' is $$-O-\phenyl-O-.$$

5. A method according to claim 1 wherein said drying oil is linseed oil.

6. A method according to claim 1 wherein n is an average of about 0.

7. A method according to claim 1 wherein about 40 to about 60% by weight diglycidyl ether is reacted with about 40 to about 60% by weight drying oil.

8. A method according to claim 1 wherein said reaction is performed under a blanket of an inert gas to exclude oxygen.

9. A method according to claim 1 including the additional step of curing said liquid modified epoxy resin.

10. A method according to claim 1 wherein said drying oil is the stochiometric reaction product of a polyhydroxy compound having 2 to 4 hydroxyl groups with a fatty acid of the formula $C_{17}H_xCOOH$ where x is 28 to 33.

11. A method according to claim 1 wherein each R is alkyl to $C_4$ and M is titanium.

12. A method according to claim 1 wherein said diglycidyl ether and said drying oil are reacted by heating at about 200° to about 250° C.

13. A method according to claim 12 wherein said diglycidyl ether and said drying oil are heated about ½ hour beyond the clear pill stage.

14. A method according to claim 1 wherein said catalyst is pre-mixed with at least one borate compound in a ratio of catalyst to borate of about 1 to 2 to about 2 to 1.

15. A method according to claim 14 wherein said catalyst and said borate compound are pre-reacted with each other.

16. A method according to claim 14 wherein said borate compound is selected from the group consisting of $$RO-B\begin{array}{c} OR \\ \backslash \\ OR \end{array}\quad \begin{array}{c} -O \\ \backslash \\ B \\ / \\ -O \end{array}\begin{array}{c} O \\ | \\ B \\ | \\ O \end{array}\begin{array}{c} O- \\ / \\ \backslash \\ O- \end{array}\quad -O-B\begin{array}{c} O \\ \backslash \\ O \end{array}R_3\begin{array}{c} O \\ / \\ O \end{array}B-O-$$

and $$\begin{array}{c} R_4 \\ \backslash \\ N \\ / \\ R_4 \end{array}\begin{array}{c} O \\ \backslash \\ B \\ / \\ R_1 \end{array}\begin{array}{c} O \\ / \\ R_1 \\ \backslash \\ O \end{array}\begin{array}{c} R_1 \\ \backslash \\ N \\ / \\ R_4 \end{array}\begin{array}{c} R_4 \\ \\ R_4 \end{array}$$

where each R is independently selected from aliphatic to $C_6$, cycloaliphatic to $C_6$, and $$-\phenyl-R_2$$

where $R_2$ is hydrogen or alkyl to $C_4$, $R_1$ is ethylene, propylene, or isopropylene, $R_3$ is a bivalent radical derived from a saturated aliphatic polyhydric alcohol having two to six hydroxyl groups two of which are removed, $R_4$ is hydrogen or R, and the open oxygen bonds are satisfied by $R_3$ or a monovalent radical derived from a monohydric alcohol having one hydroxyl group removed, selected from the group consisting of saturated and unsaturated aliphatic, aromatic, and phenolic hydroxyl alcohols.

17. A method according to claim 16 wherein said borate compound is trimetaparacresol borate.

18. A method according to claim 1 wherein said drying oil is pre-reacted with up to about 10% maleic acid, maleic anhydride, or fumaric acid, and about 1 to about 1.5 times the amount of maleic acid, maleic anhydride, or fumaric acid of at least one saturated aliphatic polyhydric alcohol having two to six hydroxyl groups.

19. A method according to claim 18 wherein said pre-reaction is in the presence of an ester-interchange catalyst.

20. A method according to claim 19 wherein said ester-interchange catalyst is lime.

21. A method according to claim 19 wherein said alcohol is pentaerythritol.

22. A method according to claim 1 wherein the fatty acid portion of said drying oil has eighteen carbon atoms.

* * * * *